United States Patent
Xu et al.

(10) Patent No.: US 9,408,811 B2
(45) Date of Patent: Aug. 9, 2016

(54) PHARMACEUTICAL COMPOSITION COMPRISING GUTTIFERONE F FOR THE TREATMENT OF PROSTATE CANCER

(71) Applicant: Hong Kong Baptist University, Hong Kong (HK)

(72) Inventors: Hongxi Xu, Hong Kong (HK); Xin Li, Hong Kong (HK); Hong Zhang, Hong Kong (HK); Yuanzhi Lao, Hong Kong (HK); Hongsheng Tan, Hong Kong (HK); Xiaoyu Wang, Hong Kong (HK); Kaixian Chen, Hong Kong (HK); Zhaoxiang Bian, Hong Kong (HK); Dajian Yang, Hong Kong (HK); Shilin Chen, Hong Kong (HK); Aiping Lu, Hong Kong (HK); Albert Sun Chi Chan, Hong Kong (HK)

(73) Assignee: Hong Kong Baptist University, Hong Kong (HK)

( * ) Notice: Subject to any disclaimer, the term of this patent is extended or adjusted under 35 U.S.C. 154(b) by 25 days.

(21) Appl. No.: 14/333,524

(22) Filed: Jul. 17, 2014

(65) Prior Publication Data
US 2015/0025155 A1    Jan. 22, 2015

Related U.S. Application Data

(60) Provisional application No. 61/847,748, filed on Jul. 18, 2013.

(51) Int. Cl.
| | |
|---|---|
| *C07C 33/38* | (2006.01) |
| *C07C 35/23* | (2006.01) |
| *A61K 31/122* | (2006.01) |
| *A61K 36/38* | (2006.01) |

(52) U.S. Cl.
CPC .............. *A61K 31/122* (2013.01); *A61K 36/38* (2013.01); *A61K 2236/00* (2013.01)

(58) Field of Classification Search
CPC ................................ C07C 33/38; C07C 35/23
USPC .................................................. 568/811, 820
See application file for complete search history.

(56) References Cited

FOREIGN PATENT DOCUMENTS

| CN | 101805352 A | 8/2010 |
|---|---|---|
| KR | 1005173 | * 1/2011 |

OTHER PUBLICATIONS

Jordan, V. C. Nature Reviews: Drug Discovery, 2, 2003, 205.*
Hackam, et al. JAMA, 296(14), 2006, 1731-1732.*
Nguyen, et al. Tetrahedron Letters, 2012, 53(34), 4487-4493.*
R. Siegel et al., "Cancer statistics, 2013," CA Cancer J Clin, 63:11-30, 2013.
V. J. Gnanapragasam et al., "Androgen receptor signalling in the prostate," BJU International,86, 1001-1013, 2000.
M. Papaioannou et al., "The natural compound atraric acid is an antagonist of the human androgen receptor inhibiting cellular invasiveness and prostate cancer cell growth," J Cell Mol Med, vol. 13, No. 8B, pp. 2210-2223, 2009.
V. Reutrakul et al., "Cytotoxic and anti-HIV-1 caged xanthones from the resin and fruits of garcinia hanbury," Planta Med, 73: 33-40, 2007.
Q. B. Han et al., "Caged garcinia xanthones: development since 1937," Current Medicinal Chemistry, 16, 3775-3796, 2009.
Q. B. Han et al., "Cytotoxic Polyprenylated Xanthones from the Resin of Garcinia hanburyi," Chem Pharm Bull, 54(2), 265-267, 2006.
V. Rukachaisirikul et al., "Antibacterial caged-tetraprenylated xanthones from the stem bark of garcinia scortechinii," Planta Med, 71: 165-170, 2005.
P. D. Sampath et al., "Mitigation of mitochondrial dysfunction and regulation of eNOS expression during experimental myocardial necrosis by alpha-mangostin, a xanthonic derivative from garcinia mangostana," Drug and Chemical Toxicology, 32(4): 344-352, 2009.

(Continued)

*Primary Examiner* — Douglas M Willis
(74) *Attorney, Agent, or Firm* — Ella Cheong Hong Kong; Sam T. Yip (57) ABSTRACT

Prostate cancer is the most commonly diagnosed cancer in males and one of the leading causes of cancer death. Although treatment options have increased for some patients, overall progress has been modest. Thus, there is a great need to develop new treatments. This invention relates to a method for treating cancer comprising using an anti-cancer compound of formula (I):

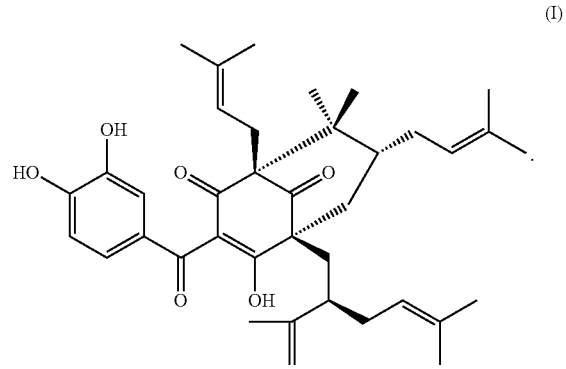

More particularly, it relates to said anti-prostate cancer compound that can be isolated from *Garcinia esculenta* or chemically synthesized and its specific anticancer/antitumor activity. The invention has a specific application in treating human prostate cancer.

8 Claims, 6 Drawing Sheets

(56) References Cited

OTHER PUBLICATIONS

S. Kasibhatla et al., "A role for transferrin receptor in triggering apoptosis when targeted with gambogic acid," PNAS, vol. 102, No. 34, 12095-12100, 2005.

M. K. Pandey et al., "Gambogic acid, a novel ligand for transferrin receptor, potentiates TNF-induced apoptosis through modulation of the nuclear factor -kB signaling pathway," Blood, 110: 3517-3525, 2007.

Y. Yang et al., "Differential apoptotic induction of gambogic acid, a novel anticancer natural product, on heptaoma cells and normal hepatocytes," Cancer Letters, 256, 259-266, 2007.

J. Yu et al., "Gambogic acid-induced G2/M phase cell-cycle arrest via disturbing CDK7-mediated phosphorylation of CDC2/p34 in human gastric carcinoma BGC-823 cells," Carcinogenesis, vol. 28, No. 3, pp. 632-638, 2007.

D. Zhai et al., "Gambogic acid is an antagonist of antiapoptotic Bcl-2 family proteins," Mol Cancer Ther, 7:1639-1646, 2008.

Q. Li et al., "Gambogenic acid inhibits proliferation of A549 cells through apoptosis-inducing and cell cycle arresting," Biol Pharm Bull, 33(3), 415-420, 2010.

Q. Qi et al., "Anti-invasive effect of gambogic acid in MDA-MB-231 human breast carcinoma cells," Biochem Cell Biol, 86: 386-395, 2008.

T. Yi et al., "Gambogic acid inhibits angiogenesis and prostate tumor growth by suppressing vascular endothelial growth factor receptor 2 signaling," Cancer Res, 68: 1843-1850, 2008.

Z. Q. Qu et al., "Gambogic acid inhibits proliferation of human lung carcinoma SPC-A1 cells in vivo and in vitro and represses telomerase activity and telomerase reverse transcriptase mRNA expression in cells," Biol Pharm Bull, 27 (11), 1769-1774, 2004.

Q. Guo et al., "Toxicoloogical studies of gambogic acid and its potential targets in experimental animals," Basic & Clinical Pharmacology & Toxicology, 99, 178-184, 2006.

Q. Qi et al., "Studies on the toxicity of gambogic acid in rats," Journal of Ethanopharmacology, 117, 433-438, 2008.

R. W. Fuller et al., "Guttiferone F, the first prenylated benzophenone from Allanblackia stuhlmannii," J Nat Prod, 62, 130-132, 1999.

K. H. Elstein et al., "Comparison of cellular and nuclear flow cytometric techniques for discriminating apoptotic subpopulations," Experimental Cell Research, 211, 322-331, 1994.

S. Reagan-Shaw et al., "Dose translation from animal to human studies revisited," The FASEB Journal, vol. 22, 659-661, 2007.

* cited by examiner

PHARMACEUTICAL COMPOSITION COMPRISING GUTTIFERONE F FOR THE TREATMENT OF PROSTATE CANCER

CROSS-REFERENCE TO RELATED APPLICATION

The present application claims benefit from the U.S. provisional patent application Ser. No. 61/847,748 filed Jul. 18, 2013, and the disclosure of which is incorporated herein by reference in its entirety.

FIELD OF INVENTION

This invention relates to a method for treating cancer using an anti-cancer compound. More particularly, it relates to an anti-prostate cancer compound that can be isolated from *Garcinia esculenta* or chemically synthesized and its specific anti-cancer/anti-tumor activity. The anti-cancer compound of the present invention has a specific application in treating human prostate cancer.

BACKGROUND OF INVENTION

Prostate cancer is the most commonly diagnosed cancer in males and one of the leading causes of cancer death in the United States. The most common therapeutic option for prostate cancer is androgen ablation, via surgical or medical castration, and chemotherapy because early tumors are androgen dependent. Another option is treatment with antiandrogens (androgenantagonists), which can block the androgen receptor-mediated gene transactivation. Therefore, in current treatments, steroidal antiandrogensare applied. However, advanced prostate cancer is resilient to most treatments. Thus, more effective therapies that can cure localized tumors and prevent their metastasis are urgently needed.

*Garcinia* species (Family Guttiferae) are tropical evergreen trees and shrubs that are widely distributed in Southeastern Asia and their phytochemistry has been widely studied. Classic and caged xanthones have been isolated from various parts of these plants, and identified as their major bioactive components. Traditionally, *Garcinia* resin (called gamboge) has been used in folk and Chinese medicine to promote detoxification and treat inflammation and wounds, and recently xanthones isolated from various *Garcinia* species also showed antibacterial, antioxidant, antiviral and neuroprotective effects.

In the last decade, most of the research on *Garcinia* species has focused on the anticancer activity of gambogic acid (GA), a caged xanthone found at high concentrations in gamboge. GA has been involved in the injectable antitumor drug since the 1970s. In 2004, GA has been granted permission for testing in clinical trial as a wide spectrum antitumor drug. GA and its derivatives are cytotoxic in many cancer cell lines by binding to the transferrin receptor and induction of G2/M cell cycle arrest and mitochondrial and death receptor-mediated apoptosis. GA also reduces invasion and angiogenesis, telomerase mRNA expression and activity and tumor volume in vivo. However, the antitumor effect of GA is not selective and it induces toxicity to the liver and kidney, which limits its development into a clinically useful anticancer drug.

Due to the toxicity of GA, there is a present need in the art to focus on the discovery of more selective compounds isolated from various *Garcinia* species.

Citation or identification of any reference in this section or any other section of this application shall not be construed as an admission that such reference is available as prior art for the present application.

SUMMARY OF INVENTION

Accordingly, one objective of this invention is to provide a method for treating cancer comprising using an anti-cancer compound with the following formula:

(I)

which can be used specifically for treating human prostate cancer.

In accordance with one aspect of the present invention, there is provided a method for treating human prostate cancer comprising using the compound of formula (I), or chemically named as Guttiferone F. The compound of the present invention can be isolated from *Garcinia esculenta* or chemically synthesized. A therapeutically effective amount of the presently claimed compound for effectively treating human prostate cancer is also provided in the present invention. In one embodiment, the therapeutically effective amount of said compound ranges from 0.81 mg/kg to 2.4 mg/kg to body weight of said subject and is administered at least once every two days. Said subject includes but not limited to human. In another embodiment, the therapeutically effective amount of said compound is from 1.62 mg/kg to 2.4 mg/kg to body weight of said subject and is administered at least once every two days without calorie restriction. In yet another embodiment, the therapeutically effective amount of said compound ranges from 0.81 mg/kg to 1.2 mg/kg to body weight of said subject and is administered at least once every two days with calorie restriction. The therapeutically effective amount of the presently claimed compound can be administered to a subject through different route which includes but not limited to oral, intraperitoneal, intravenous, intratumoral, and/or subcutaneous route.

Another objective of the present invention is to provide a method for preparing a composition comprising a therapeutically effective amount of the compound of formula (I). In one embodiment, the compound of the present invention, which is Guttiferone F (or as "GF" hereinafter), can be isolated from *Garcinia esculenta*. In the same embodiment, the presently claimed compound is prepared according to the following procedure:

(a) air-dried and powdered twigs of 4 kg plant materials of *Garcinia esculenta* are extracted with 5×20 L petroleum ether at every two days to result in multiple extracts;

(b) multiple extracts from step (a) are combined and the combined extracts are evaporated to dryness under vacuum to give fraction I at 40 g;

(c) 37 g of fraction I from step (b) is chromatographed on a silica gel column using a gradient of petroleum ether—EtOAc (100:0 to 50:50, v/v), yielding fifteen fractions: IA to IO;

(d) Fraction IL is selected from the fifteen fractions of (c) and further chromatographed on MCI gel eluted successively with 90% and 100% EtOH to afford two subfractions, IL1 and IL2;

(e) Only subfraction IL1 from step (d) at 10.5 g is subjected to reverse-phase C18 silica gel CC, eluted in a step gradient manner with MeOH—$H_2O$ in a ratio from 70:30 to 100:0 in order to yield 350 mg of said compound.

A further objective of the present invention is to provide a composition comprising the therapeutically effective amount of the compound of formula (I) in order to specifically treat prostate cancer or inhibit the associated tumor growth in a subject administered according to the dosage regime disclosed in the present invention. The dosage regime may include but not limited to the administration of the therapeutically effective amount of the compound of formula (I) at least once every two days, e.g. daily, and with or without calorie restriction. Said composition can be administered via different route including but not limited to oral, intraperitoneal, intravenous, intratumoral, and/or subcutaneous route. In one embodiment, a therapeutically effective amount of the compound of formula (I) in said composition is from 0.81 mg/kg to 2.4 mg/kg to body weight of said subject at each time of administration. Time course of the administration may be for about 3 weeks or for at least 18 days.

Those skilled in the art will appreciate that the invention described herein is susceptible to variations and modifications other than those specifically described.

The invention includes all such variation and modifications. The invention also includes all of the steps and features referred to or indicated in the specification, individually or collectively and any and all combinations or any two or more of the steps or features.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the invention and apply throughout. Unless otherwise defined, all other technical terms used herein have the same meaning as commonly understood to one of ordinary skill in the art to which the invention belongs.

Other aspects and advantages of the invention will be apparent to those skilled in the art from a review of the ensuing description.

BRIEF DESCRIPTION OF DRAWINGS

The above and other objects and features of the present invention will become apparent from the following description of the invention, when taken in conjunction with the accompanying drawings, in which.

DETAILED DESCRIPTION OF INVENTION

The present invention is not to be limited in scope by any of the specific embodiments described herein. The following embodiments are presented for exemplification only.

This invention have screened various components using different cancer cells, and found that prenylated benzophenones have potent cytotoxic effects on human prostate cancer cell lines. In this invention, Guttiferone F is found to be one of the prenylated benzophenones which could inhibit the growth of prostate cancer by apoptosis most significantly. In one of the animal studies of the present invention, intratumor administration of Guttiferone F is shown to effectively inhibit prostate cancer growth in nude mice. Other administration routes such as intraperitoneal injection are also shown to be effective for Guttiferone F to inhibit the growth of tumor or kill the human prostate cancer cells in the same animal model. Thus, Guttiferone F can be developed as an anticancer drug against prostate cancer.

Example 1

Extraction, Isolation and Identification

Figure 1:
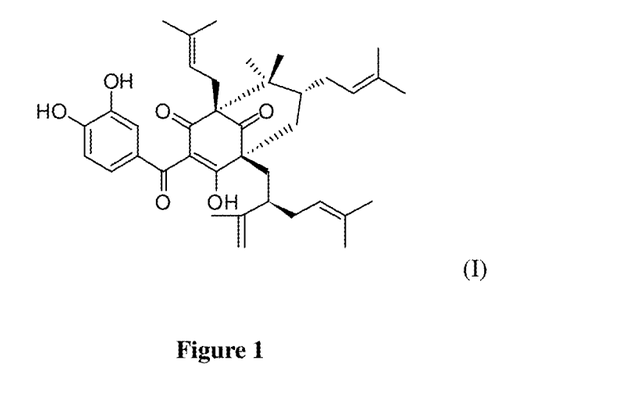
FIG. 1 shows the structure of the anti-cancer compound, formula (I), or named as Guttiferone F.

This example is one of the embodiments in the present invention to isolate Guttiferone F from *Garcinia esculenta* in order to prepare a pharmaceutically acceptable compound for treating human prostate cancer, but is not intended to limit to said plant. In this example, air-dried and powdered twigs of the plant (4 kg) of *Garcinia esculenta* are extracted with petroleum ether (5×20 L, two days each). Multiple extracts with the petroleum ether are combined and the combined extracts are evaporated to dryness under vacuum to give fraction I (40 g). The remaining materials are refluxed with 80% EtOH (v/v, 5×20 L). Multiple extracts from these remaining materials after reflux with the 80% EtOH are combined and the combined extracts are evaporated to dryness under vacuum, and the residue is suspended in $H_2O$ (5 L) and extracted with EtOAc (5×5 L) to give fractions II (50 g, EtOAc soluble) and III (the aqueous fraction), respectively. The remaining materials after extraction with the EtOAc to give fractions II and III are further refluxed with distilled water (5×20 L) to give a water-soluble fraction (IV). Fraction I (37 g) is chromatographed on a silica gel column (CC) using a gradient of petroleum ether—EtOAc (100:0 to 50:50, v/v) guided by TLC, yielding fifteen more fractions (Fraction IA-IO). Fraction IL is selected from the fifteen fractions and further chromatographed on MCI gel eluted successively with 90% and 100% EtOH to afford two subfractions (IL1 and IL2). Fraction IL1 (10.5 g) is subjected to reverse-phase C18 silica gel CC, eluted in a step gradient manner with MeOH—$H_2O$ (70:30 to 100:0) to yield Guttiferone F (350 mg). The structure of Guttiferone F is elucidated as shown (FIG. 1) by comparison of their spectroscopic data with published data. The purity of Guttiferone F is checked by UPLC-DAD and the result displays that the purity is above 98%.

Example 2

In vitro Studies of Guttiferone F on Different Cancer Cells (I) Cell Culture

Two human prostate cancer cell lines LNCaP and PC3 are maintained in RPMI1640 (Sigma Chemical Company, St. Louis, Mo., USA) supplemented with 10% fetal bovine serum (HyClone). Hepatocellular carcinoma cell line Hep G2, epithelial cervical cancer cell line HeLa and nasopharyngeal carcinoma cell line CNE are maintained in DMEM (Invitrogen) supplemented with 10% new-born calf serum (Gibco), 100 U/ml penicillin and 100 μg/ml streptomycin (Invitrogen). All cancer cells are maintained in a humidified atmosphere containing 5% $CO_2$ at 37° C.

(II) Assessment of Anti-Cancer Activity

MTT Assay

Different cancer cells are seeded in a 96-well plate and pre-incubated for 24 hours before treatment with Guttiferone F (0-50 μM). After 48 h of treatment, 10 μl of MTT solution (5 mg/ml) (Sigma Chemical Company, St. Louis, Mo., USA) are added to each well and incubated for 4 h. The resulting crystals are dissolved in DMSO. The controls include native cells and medium only. The spectrophotometric absorbance at 570 nm is measured using a microplate reader (Synergy HT, Bio-Tek Instruments Inc., Winooski, Vt., USA). The percentage cytotoxicity is calculated by the formula: Percentage cytotoxicity (cell death)=[1-(absorbance of experimental wells/absorbance of control wells)]×100%. As shown in Table 1, Guttiferone F could inhibit different cell lines selectively, revealing that Guttiferone F is more specific to human prostate cancer than the others under this assay.

TABLE 1

Cytotoxic assay of Guttiferone F in different cell lines

| Cell lines | $IC_{50}$ (μM) |
|---|---|
| LNCaP | 5.17 ± 0.20 |
| PC-3 | 12.64 ± 3.01 |

TABLE 1-continued

Cytotoxic assay of Guttiferone F in different cell lines

| Cell lines | $IC_{50}$ (μM) |
|---|---|
| Hep G2 | 32.93 ± 1.56 |
| HeLa | 13.13 ± 1.32 |

(III) Flow Cytometry

Based on the result of the above MTT assay on prostate cancer cell lines, LNCaP cells and 10 μM of Guttiferone F are selected for studying the effect of Guittiferone F on apoptosis of human prostate cancer cells. Before that, LNCaP cells are treated with Guttiferone F at the concentration of 10 μM. Cells are trypsinized and fixed in ice-cold 100% methanol overnight at 4° C. Cells are washed, stained with propidium iodide (PI) for overnight, and subjected to fluorescence activated cell sorting (FACS) analysis on a FAC Scan flow cytometer (BD PharMingen, USA). Data are analyzed using the WinMID software.

Figure 2:
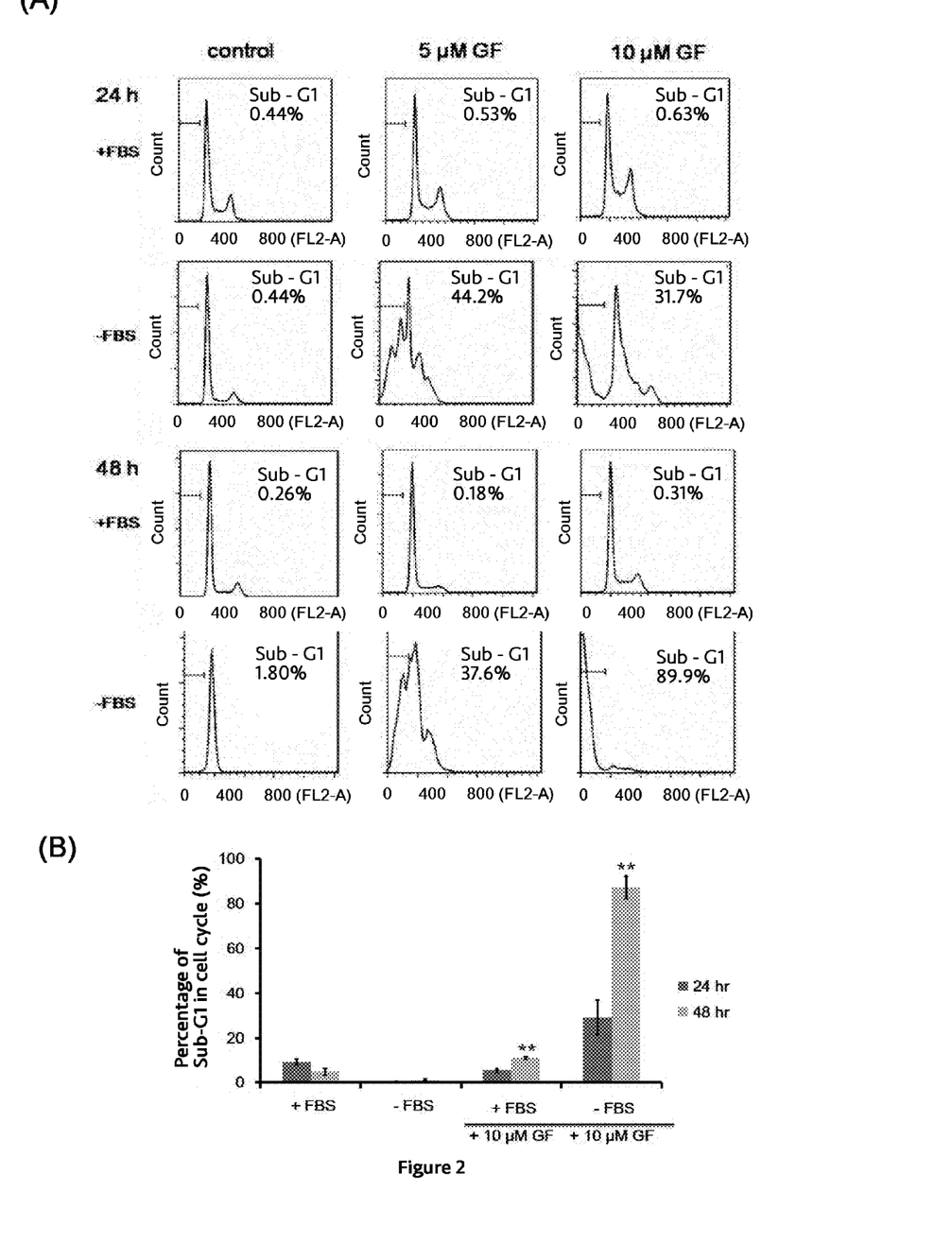
FIG. 2 shows (A) histograms of FACS analysis and (B) percentage of sub-G1 phase of a human prostate cancer cell lines cell line, LNCaP, which the cells are treated with 0 µM (control), 5 µM and 10 µM Guttiferone F for 24 h and 48 h. *Significant (<0.05); **highly significant (p<0.001)

To detect the apoptosis, sub-G1 phase cells were measured. Such cells are usually considered to be the result of apoptotic DNA fragmentation. The DNA is degraded by cellular endonucleases, during apoptosis. Therefore, nuclei of apoptotic cells contain less DNA than nuclei of healthy G0/G1 cells, resulting in a sub-G1 peak in the fluorescent histogram that may be used to determine the relative amount of apoptotic cells. FIG. 2 shows that 10 μM Guttiferone F can induce LNCaP cell death by apoptosis significantly in serum-free medium at a time dependent manner.

(IV) Change in Mitochondria and Nucleus DNA

Figure 3:
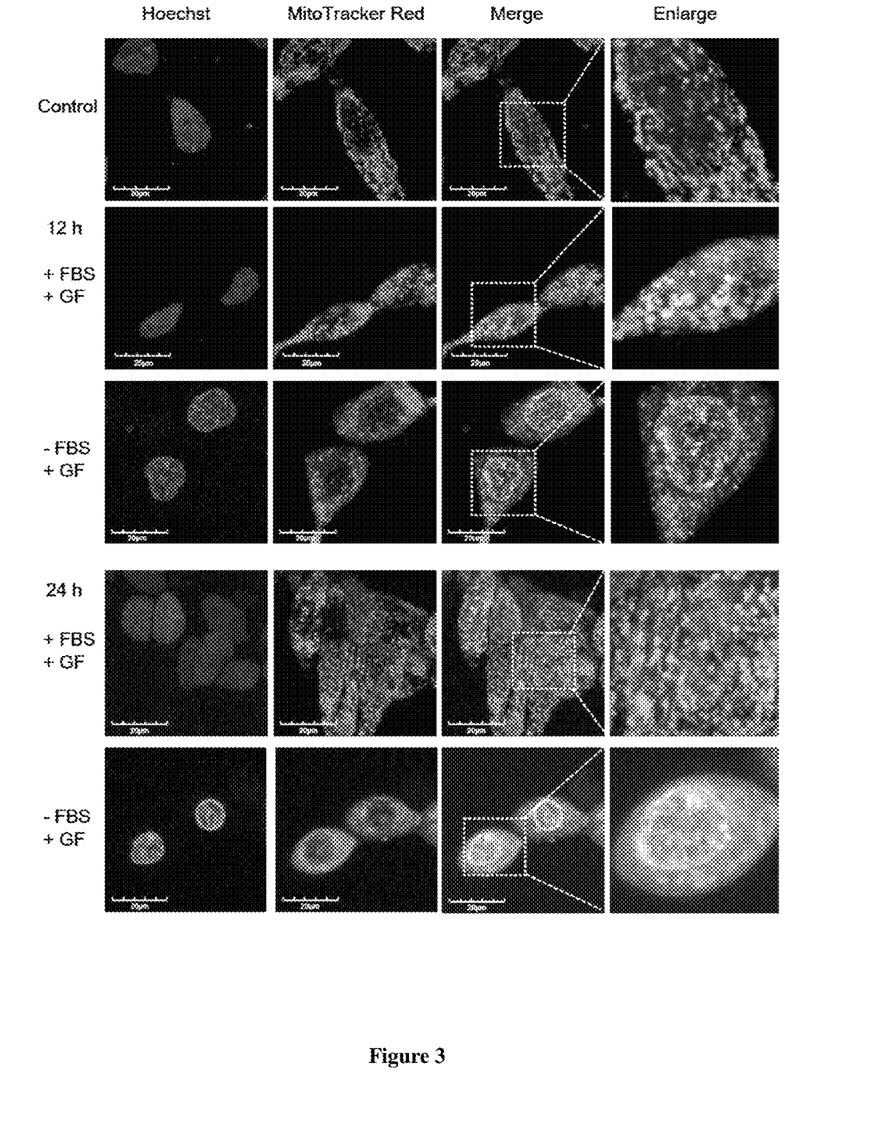
FIG. 3 shows laser scanning confocal microscopy images (60× objective lens) of LNCaP cells stained with Hoechst 33258 and MitoTracker Red. Hoechst is depicted as blue in the first column of images while MitoTracker Red is depicted as red in the second column of images; double stain of Hoechst 33258 and MitoTacker Red is shown in the third column of images, in which the dotted square in each image represents the area where the part is enlarged; the corresponding enlarged area of the image from the third column is shown in the fourth column.

LNCaP cells (2×$10^5$) are seeded on 35 mm culture dish and incubated 24 h to allow attachment. After the different treatment of Guttiferone F for 12 h or 24 h, the medium is removed from the dish and the staining solution (50 μg/ml Hoechst 33258 and 1 ng/ml MitoTracker Red in PBS) is added. The fluorescence of the bound dyes is analyzed using a laser scanning confocal microscope (FV10i, Olympus Corporation, Japan). FIG. 3 shows that DNA fragmentation and mitochondria focus are visualized under laser confocal microscopy.

Example 3

Figure 4:
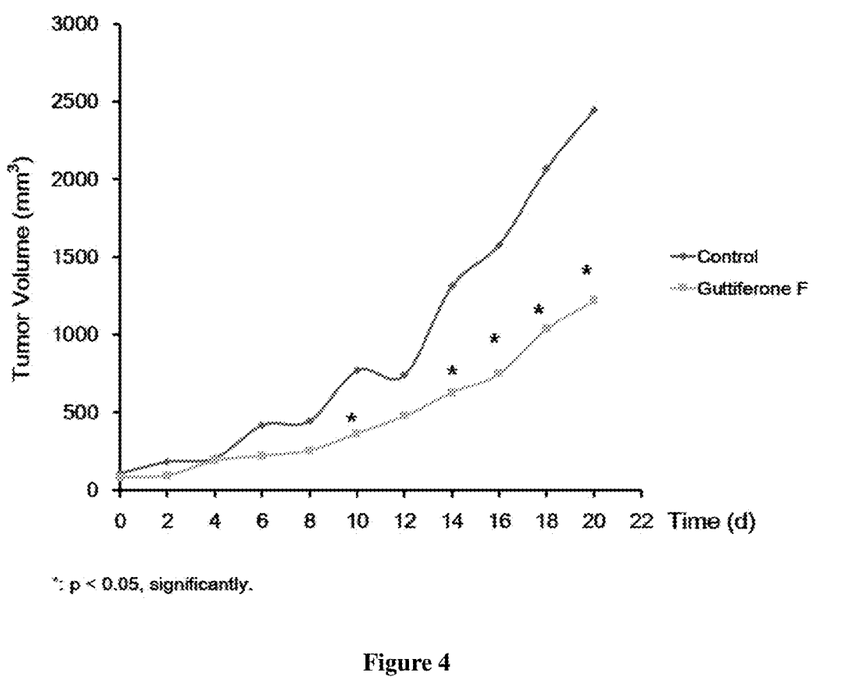
FIG. 4 shows the tumor volume changes in PC3 control and Guttiferone F (intratumoral injection, 100 µM) treatment groups of a disease mouse model. *Significant (p<0.05)

In Vivo Studies of Guttiferone F on Inhibition of Tumor Growth in Xenograft Nude Mouse Model A A total of 1×$10^6$ PC3 cells suspended in 100 μl of PBS and 100 μl of Matrigel (BD Biosciences, Bedford, Mass.) are inoculated subcutaneously (s.c.) into the right flank of six 4-week-old male nude mice. Drug injections are made once the tumors reach an average volume of about 100 $mm^3$. Mice are divided randomly into two groups of 3 mice in each group and subjected to intratumoral injection of vehicle (control) or 20 mM Guttiferone F every two days for 20 days. (After 20 μM GF for 3 times, the dosage is increased to 100 μM GF). Tumor volume is measured by calipers and calculated by V=L×$W^2$/2 at different time intervals. For intratumoral injection, 20 mM Guttiferone F is prepared in 5% dimethyl sulfoxide, 5% tween 80, and 90% PBS. As shown in FIG. 4, the growth of tumor is inhibited significantly after 14 days.

Effect of Caloric Restriction on Enhancing Anticancer Activity Of Guttiferone F In Vivo (Nude Mouse Model B)

Figure 5:
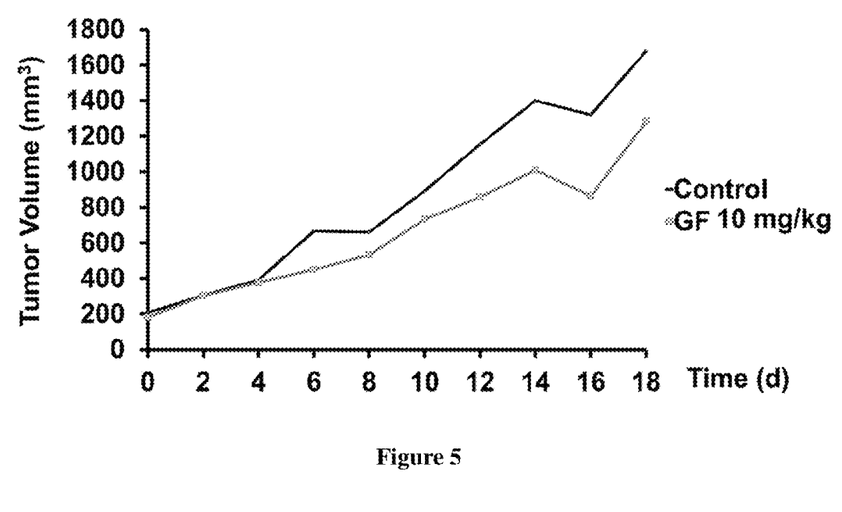
FIG. 5 shows the tumor volume changes in PC3 control and Guttiferone F (daily intraperitoneal injection, 10 mg/kg) treatment groups of a disease mouse model.

A total of 1×$10^6$ PC3 cells suspended in 100 μl of PBS and 100 μl of Matrigel are inoculated subcutaneously into the right flank of six 4-week-old male nude mice. Drug injections are made once the tumors reach an average volume of about 200 mm³. Mice are divided randomly into two groups of 7 for each group and subjected to intraperitoneal injection of vehicle or 10 mg/kg Guttiferone F every two days for 18 days. Tumor volume is measured by calipers and calculated by V=L×W²/2. For intratumoral injection, Guttiferone F is prepared in 5% dimethyl sulfoxide, 5% tween 80, and 90% PBS. As shown in FIG. 5, the growth of tumor is not inhibited significantly in 18 days.

Figure 6:
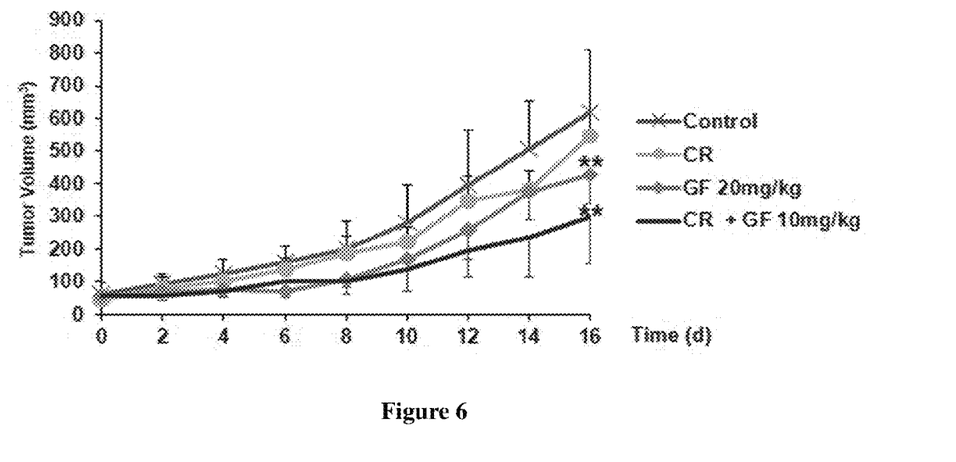
FIG. 6 shows the tumor volume changes in PC3 control and Guttiferone F (daily intraperitoneal injection, 20 mg/kg; or caloric restriction+ daily intraperitoneal injection, 10 mg/kg) treatment groups of a disease mouse model. ** Highly significant (p<0.01)

Four-week-old male BALB/c nude mice from the Experimental Animal Center of Chinese Academy of Science (Shanghai, China) are used in this example. Approximately 1×10⁶ PC3 cells suspended in 100 µl of PBS and 100 µl of Matrigel are injected subcutaneously into the right side of the animals. One week later, 28 mice bearing tumors around 50 mm³ in volume are randomly divided into four groups (n=7 per group): Group 1: Control (normally fed, receiving daily i.p. vehicle), Group 2: Caloric restriction (fed with 70% of their normal food intake, receiving daily i.p. vehicle), Group 3: GF (normally fed, receiving daily i.p. 20 mg/kg of GF), and Group 4: GF+caloric restriction (calorie-restricted mice receiving daily i.p. 10 mg/kg of GF). Mice are administered via intraperitoneal injection of vehicle (control) in a form of solvent (0.5% DMSO, 0.5% Tween-80 in saline) and GF at the dose of 10 mg/kg or 20 mg/kg in 200 µl vehicle once every other day. As shown in FIG. 6, tumor volume increases dramatically in the control group, whereas tumor growth is significantly less prominent in GF-treated mice after 8 days. Using the conversion formula between animal dose and human dose taught in Regan-Shaw et al. (2007), the daily human dose of GF through intraperitoneal injection is about 1.62 mg/kg to 2.4 mg/kg (corresponding to 20 mg/kg of GF for mouse); the daily human dose of GF under calorie restriction is at least in a range of 0.81 mg/kg to 1.2 mg/kg (corresponding to 10 mg/kg of GF for mouse).

Plant Material

*Garcinia esculenta* Y. H. Li twigs are collected in August 2010 in Nujiang, Yunnan Province, People's Republic of China. Plant material was identified by Prof. Yuanchuan Zhou, Yunnan University of Traditional Chinese Medicine. A voucher specimen (Herbarium No. 20100801) has been deposited at the Innovative Research Laboratory of TCM, Shanghai University of Traditional Chinese Medicine.

INDUSTRIAL APPLICABILITY

This invention provides an anti-cancer compound, Guttiferone F, and shows its anti-prostate cancer effects. In summary, Guttiferone F can be further developed as an anticancer drug against prostate cancer.

What is claimed is:

1. A method for inhibiting prostate cancer tumor growth in a human, comprising administering to said human a therapeutically effective amount of a pharmaceutical composition comprising a compound of formula (I):

and a pharmaceutically acceptable carrier, excipient and/or adjuvant.

2. The method of claim 1, wherein said therapeutically effective amount is equal to or greater than 0.81 mg/kg to body weight of said human.

3. The method of claim 1, wherein said therapeutically effective amount is from 0.81 mg/kg to 2.40 mg/kg to body weight of said human.

4. The method of claim 1, wherein said therapeutically effective amount is from 0.81 mg/kg to 1.20 mg/kg to body weight of said human.

5. The method of claim 1, wherein said pharmaceutical composition is administered to said human via one or more routes selected from the group consisting of subcutaneous, intratumoral, intraperitoneal, intravenous and oral.

6. The method of claim 1, wherein said pharmaceutical composition is administered at least once every two days to said human.

7. The method of claim 1, wherein said pharmaceutical composition is administered daily to said human.

8. The method of claim 1, wherein said human is under caloric restriction.

* * * * *